United States Patent [19]
Roth et al.

[11] Patent Number: 4,929,233
[45] Date of Patent: May 29, 1990

[54] IMPLANTABLE FLUID IMBIBING PUMP WITH IMPROVED CLOSURE

[75] Inventors: Nathan Roth, San Francisco; Su I. Yum, Los Altos, both of Calif.

[73] Assignee: ALZA Corporation, Palo Alto, Calif.

[21] Appl. No.: 236,974

[22] Filed: Aug. 26, 1988

[51] Int. Cl.⁵ .............................................. A61M 5/00
[52] U.S. Cl. .................................. 604/131; 604/892.1
[58] Field of Search .......................... 604/131, 892.1; 215/320; 220/306

[56] References Cited

U.S. PATENT DOCUMENTS

| | | | |
|---|---|---|---|
| 3,672,528 | 6/1972 | Faulstich | 215/46 A |
| 3,760,984 | 9/1973 | Theeuwes | 222/95 |
| 3,858,742 | 1/1975 | Grussen | 215/320 |
| 3,885,695 | 5/1975 | Schaefer | 215/224 |
| 3,987,790 | 10/1976 | Eckenhoff et al. | 128/260 |
| 3,995,631 | 12/1976 | Higuchi et al. | 128/260 |
| 4,034,756 | 7/1977 | Higuchi et al. | 128/260 |
| 4,037,746 | 7/1977 | Ver Hage | 215/31 |
| 4,037,748 | 7/1977 | Stubbs | 215/320 X |
| 4,057,160 | 11/1977 | Victor et al. | 215/320 X |
| 4,281,774 | 8/1981 | Mumford | 220/306 |
| 4,320,758 | 3/1982 | Eckenoff et al. | 604/892.1 |
| 4,474,575 | 10/1984 | Eckenhoff et al. | 604/131 |
| 4,539,004 | 9/1985 | Eckenhoff et al. | 604/131 |
| 4,625,876 | 12/1986 | Bullock III | 215/256 |

FOREIGN PATENT DOCUMENTS 1432241 12/1968 Fed. Rep. of Germany ...... 215/320

*Primary Examiner*—Dalton L. Truluck
*Attorney, Agent, or Firm*—D. Byron Miller; Steven F. Stone; Edward L. Mandell

[57] ABSTRACT

An improved imbibing agent dispenser having a snap-on closure which is highly reliable, is simple to assemble on one end of the agent dispenser, and can be made at minimum expense without requiring heat or an adhesive to bond the closure to the dispenser. The closure is held in place on the dispenser by a locking feature formed by a shoulder on the end of the dispenser and a ledge on an outer, annular wall of the closure, the ledge being removably hooked beneath and biased toward the shoulder to releasably lock the closure to the dispenser. An important aspect of this closure is that the design provides for the complete containment of a solute component within the dispenser.

26 Claims, 2 Drawing Sheets

IMPLANTABLE FLUID IMBIBING PUMP WITH IMPROVED CLOSURE

BACKGROUND OF THE INVENTION

Field of the Invention

This invention relates to improvements in agent dispensers in the form of fluid imbibing pumps and, more particularly, to an implantable agent dispenser having an improved closure.

This invention relates to fluid imbibing osmotic pumps of the type described in U.S. Pat. Nos. 3,760,984, 3,977,790, 3,995,631, 4,034,756, 4,474,575 and 4,539,004, all of which are incorporated herein by reference. An agent dispenser which is osmotically driven is disclosed in each of these patents. Such an agent dispenser is capable of having a size which renders it suitable for use as a therapeutic device for administering agents, particularly drugs to animals and humans when the agent dispenser is exposed to body fluids on the skin, under the skin or in a body cavity such as the gastrointestinal tract or the vagina, for example.

An agent dispenser of the type described includes the following components: an outer membrane, at least a portion of which is permeable to fluids, such as water; an inner agent receiving means, such as a flexible bag that holds a flowable agent to be dispensed; and an intermediate fluid imbibing means such as a layer of an osmotically effective solute composition, such as an inorganic salt. A discharge port is provided for the bag to allow the agent contained therein to be directed out of the bag and to a point of use.

Actuation of the agent dispenser is achieved after an agent has been directed into the bag and the agent dispenser has been in an environment, such as on the skin, below skin level, or in a body cavity. Body liquids are imbibed from the environment by the solute through the membrane and into the space between the inner bag and the membrane. The imbibed water squeezes and collapses the bag, thereby causing the agent in the bag to be forced out of the bag through and out of the discharge port.

There are numerous problems associated with state of the art dispensers such as the expense and difficulties in manufacturing. However, the major problem with the implantable agent dispensers of conventional design is that there is no assurance that the agent dispenser will not disassemble during use. Upon disassembly, the agent in the dispenser will be dispensed at a much greater rate than is desirable or safe; thus, a need exists for an improved, implantable fluid imbibing pump which remains completely assembled at all times while in use. The present invention fulfills this need by virtue of an improved closure for closing the ends of the membrane and bag to form the agent dispenser.

DEFINITION OF TERMS

The expression "agent" as used herein denotes any drug or agent administered to produce a nutritional, therapeutic or other desired effect including for example: composition in any way affecting any biological entity; substance having a nutrient or stimulating action or growth inhibiting, destroying or any regulating action on plant growth, controlled or otherwise; substance to be assimilated by any organism, e.g., human being, animal, or lower order organism, for its nourishment or for regulating its growth; substance exhibiting any of the above activities to be directly applied to the habitat, surroundings or environment of any of the above organisms; and substance having any other effect on any other environment, especially any aqueous environment.

Therefore, suitable agents for use with the dispenser of this invention include, without limitation, those which are generally capable of:

1. Preventing, alleviating, treating or curing abnormal or pathological conditions of the living body by such means as destroying a parasitic organism or limiting the effect of the disease of abnormality by chemically altering the physiology of the host of parasite;
2. Maintaining, increasing, decreasing, limiting or destroying a physiologic body or plant function, e.g., vitamin compositions, set sterilants, fertility inhibitors, fertility promoters, growth promoters, and the like;
3. Diagnosing a physiological condition or state;
4. Controlling or protecting an environment or living body by attracting, disabling, inhibiting, killing, modifying, repelling or retarding an animal or microorganism, such as food and non-food baits, attractants and lures, biocides, pesticides, algicides, parasiticides, rodenticides, insecticides, fungicides, and the like;
5. Preserving, disinfecting or sterilizing; and
6. Controlling or affecting generically an environment, as by introducing a catalyst or metering a reactant into a reacting chemical system, or by effecting any chemical process therein, such as a fermentation, including propagation and/or attenuation of a microorganism.

The term "environment" as used herein denotes any prospective situs for the dispenser of this invention, or at least for the external fluid permeable membrane component thereof, which is comprised of or will provide sufficient fluid, e.g., water, for absorption into the dispenser to develop the needed osmotic pressure on which its motive force depends; and implicit in the foregoing definition of "agent"—one that will develop its action in the presence of such an environment, or one that will develop its action on a remote and/or another environment, which need not be fluid or aqueous.

SUMMARY OF THE INVENTION

The present invention is directed to an improved agent dispenser of the type described, wherein the agent dispenser has a snap-on closure which is highly reliable, is simple to assemble on an end of the agent dispenser, and can be made at minimum expense without requiring heat or an adhesive to bond the closure to the dispenser.

The closure of the present invention is held in place on the adjacent open ends of the membrane and the bag by a locking feature formed by a shoulder on the end of the membrane and a ledge on an outer, annular wall of the closure, the ledge being removably hooked beneath and biased toward the shoulder to releasably lock the closure to the membrane. An important aspect of this closure is that the design of the closure provides for the complete containment of the solute component within the fluid dispenser.

The snap-on closure of the present invention has the following advantages:

1. The snap-on feature requires no heat or adhesive to hold the closure in place.

2. The wall having the locking ledge must be expanded to snap under the shoulder of the membrane; thus, the closure must be expanded to be removed.
3. The closure has a lateral, resilient flange which is compressed to assemble the closure to the membrane; thus, upon removal of pressure, the flange biases the wall inwardly, thereby holding the ledge firmly in place against the shoulder.
4. The closure body must be compressed to fit it in the end of the bag; thus the closure is biased outwardly against the inner surface of the bag, forming a seal and further enhancing the outer ledge lock.
5. In use as part of a fluid imbibing pump, the membrane imbibes water and the intermediate sleeve swells, thus serving to increase the locking function of the closure.

The primary object of the present invention is to provide an improved agent dispenser in the form of a fluid imbibing pump wherein the dispenser includes an improved closure which is held in place by a locking feature to thereby assure that the dispenser will not become disassembled during use.

Another object of the present invention is to provide an improved closure for an agent dispenser of the type described, wherein the resilience of the assembly is relied upon to lock the assembly in place on the open end of the dispenser, whereby the closure forms a seal which requires no heat or adhesive to keep the closure in place.

Other objects of this invention will become apparent as the following specification progresses, reference being had to the accompanying drawings for an illustration of several embodiments of the closure of the invention.

DETAILED DESCRIPTION OF THE INVENTION

Figure 1:
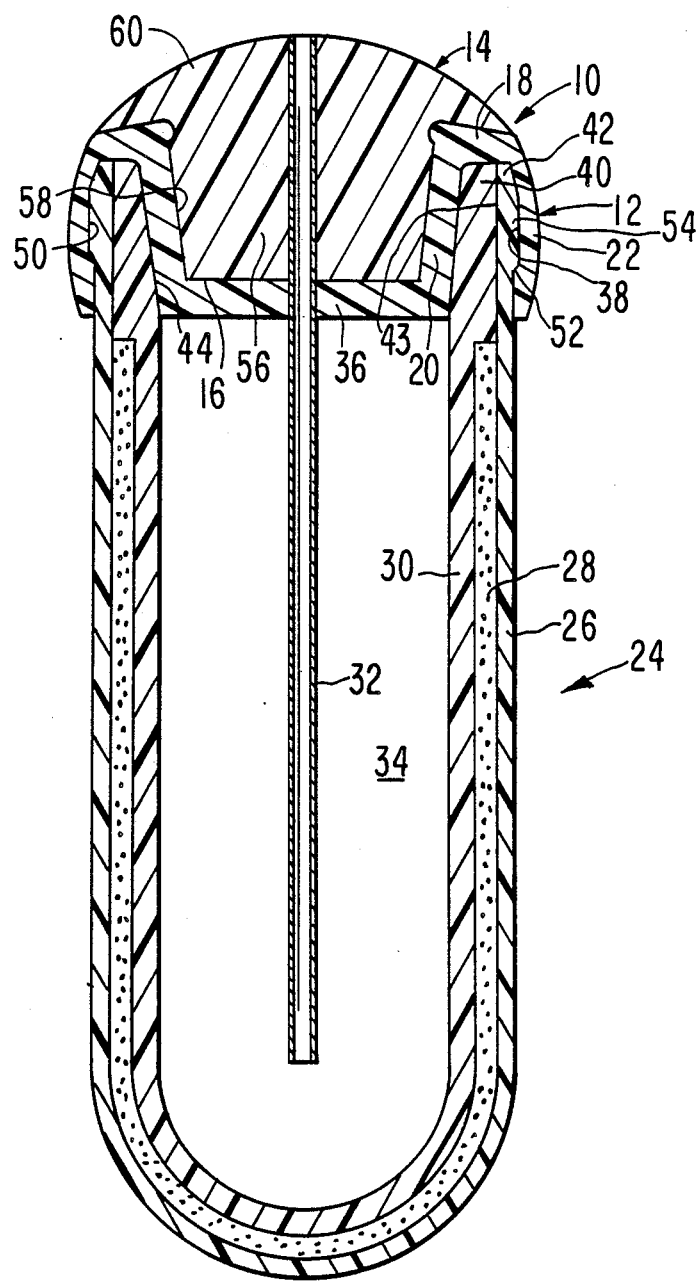
FIG. 1 is a vertical section through an agent dispenser having a first embodiment of the closure of the present invention thereon.
Figure 2:
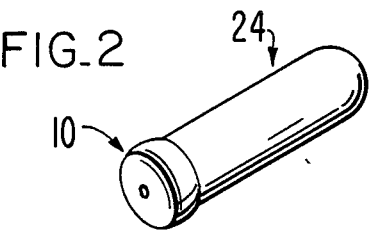
FIG. 2 is a perspective view of the agent dispenser of FIG. 1 on a reduced scale.

A first embodiment of the closure of the present invention is shown in FIGS. 1 and 2 and is denoted by the numeral 10. Closure 10 includes a cap 12 and a plug 14 which is inserted in a central recess 16 of the cap. The outer periphery of the plug overlies an annular flange 18 integral with an inner, annular wall 20 and an outer, annular wall 22 of cap 12.

Closure 10 is to be used to close the open end of an agent dispenser 24 in the form of an osmotic pump. The agent dispenser 24 includes an outer, rigid, shape-retaining casing 26 in the form of a tube at least a portion of which is a semipermeable membrane, an intermediate, fluid imbibing means such as osmotically active sleeve 28, and an inner agent receiving means such as collapsible bag 30. Membrane 26, sleeve 28 and bag 30 are tubular and are fitted together as shown in FIG. 1. They form a receptacle which is closed at the one end and open at the other end, the open end being closed by closure 10. The agent dispenser 24 is of the type described in commonly owned U.S. Pat. No. 3,987,790, 3,995,631 and 4,034,756. The agent to be dispensed is in a flowable form, preferably in a gel, paste or other semi-solid state, albeit a solution or concentrated solution of agent will sometimes suffice.

Sleeve 28 includes an osmotically effective solute, such as an inorganic salt. When fluid, typically water, is imbibed through membrane 26, it causes the solute in sleeve 28 to expand, causing bag 30 to collapse and to squeeze out the agent contained therein through the discharge tube 32 which extends into the reservoir 34 of bag 30, the upper end of the tube 32 passing through the central web 36 of cap 12 and through the center part of plug 14 as shown in FIG. 1.

All of the structural elements of agent dispenser 24 have been known and used in the past. The improvement of the first embodiment of the present invention is closure 10 comprised of cap 12 and plug 14 when used with dispenser 24. In one embodiment the cap 12, plug 14 and tube 32 are separate components. However, this invention also contemplates use of an integral closure where the cap, plug and tube are preassembled as one unit to be affixed to dispenser 24.

Annular wall 20 of cap 12 extends axially of the longitudinal axis of dispenser 24 with wall 20 being tapered outwardly as the outer flange 18 is approached. Flange 18 extends generally laterally from the outer end of wall 20. Wall 22 forms with wall 20 an annular recess 38 which receives the outer, annular end 40 of bag 30 and the outer end 42 of membrane 26. Ends 40 and 42 form an interface 43 which seals sleeve 28 between membranes 26 and 30.

The outer surface of wall 20 mates with the inner surface of end 40 to present an interface 44 which extends from the lower surface of web 36 to flange 18. A third interface 50 is formed between the outer surface of end 42 and the inner surface of wall 22. Moreover, wall 22 has a undercut ledge 52 which underlies a shoulder 54 formed at the outer surface of upper end 42 of membrane 26. This ledge and shoulder combination forms a locking means for assuring that closure 10 is locked to dispenser 24.

Since cap 12 is of a resilient material, such as rubber, plastic or the like, wall 22 is biased inwardly against interface 50 and, in turn, causing the surfaces at interfaces 43 and 44 to be biased toward each other to provide a biasing of ledge 52 and forward shoulder 54. The wall 22, when cap 14 is applied, is stretched to snap the ledge 52 under the shoulder 54 of outer end 42 of membrane 26. Thus, wall 22 must be expanded to remove the cap and plug assembly to open dispenser 24. It is to be understood that wall 22 requires no heat or adhesive to position it in place.

Plug 14 has a central body 56 with a tapered, annular, outer surface. The plug fits into recess 16 above web 36 within wall 20 of cap 12. Cap 14 is of a compressible, resilient material, such as rubber, plastic or the like and must be compressed to fit body 56 in the recess 16. Thus, body 56 forms an interface 58 with wall 20 which also contributes to the seal provided by closure 10 for the open end of dispenser 24. A dome-shaped upper part 60 integral with body 56 of plug 14 overlies flange 18 and allows tube 32 to extend through and outwardly of the dispenser 24.

To assemble the unit shown in FIG. 1, membrane 26, sleeve 28 and bag 30 are first assembled together so that ends 40 and 42 of bag 30 and membrane 26 are in face-to-face relationship to form interface 43. Then, cap 12 is put into place, forcing wall 20 against the inner surface of end 40 of bag 30, forming interface 44. When this occurs, wall 22 is forced about end 42 of membrane 26 until ledge 52 underlies shoulder 54, thus forcing flange 18 against the upper end faces of ends 40 and 42. Thus, interface 38 is formed between end 42 and the inner surface of wall 22.

Finally, plug 14 is put into place in recess 16 and presents interface 58 which is formed when body 56 is biased against the inner surface of wall 20. The plug 14 then has its body 56 biased against wall 20; wall 20 biases annular end 40 against annular end 42; and end 42 biases wall 42 upwardly and outwardly, thereby enhancing the locking means defined by ledge 52 and shoulder 54.

An agent to be dispensed can then be directed into the reservoir 34 of bag 30 through tube 32. In the alternative, the agent can be placed in the reservoir 34 before closure assembly 10 is put into place.

The closure 10 permits use on or under the skin or in a body cavity without allowing the closure to become separated from the dispenser 24. Thus, closure 10 assures continuous operation of the dispenser until the contents of bag 30 have been depleted.

Figure 3:
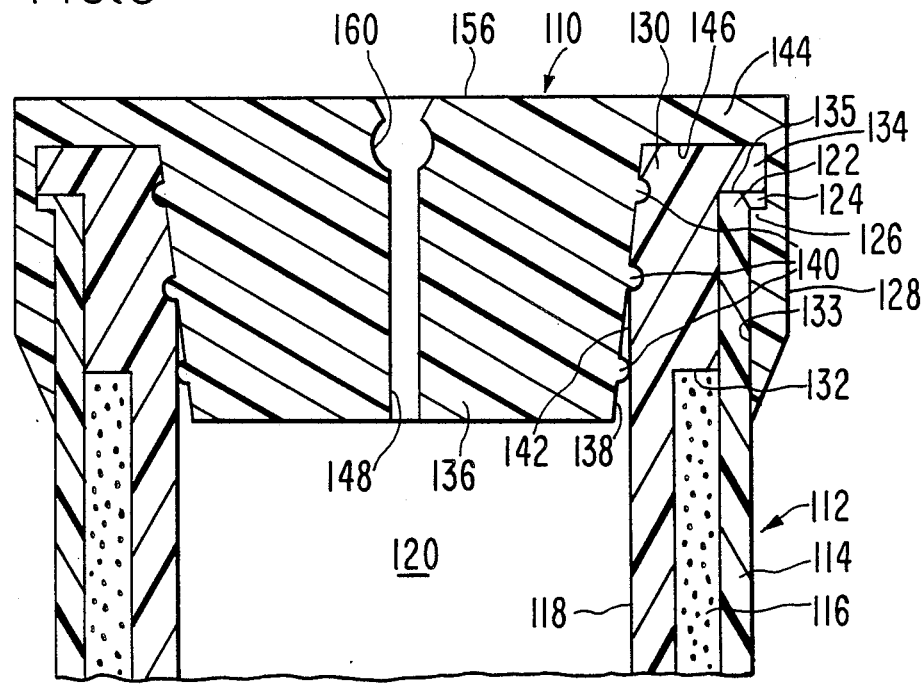
FIGS. 3 and 4 are enlarged, fragmentary, cross-sectional views of second and third embodiments of the closure.

FIG. 3 shows another form of closure denoted by numeral 110 for the outer open end of an agent dispenser 112 having an outer, shape-retaining, casing 114 at least a portion of which is a semipermeable membrane, an intermediate sleeve 116, and an inner, collapsible bag 118 presenting a reservoir 120 for receiving an agent to be dispensed, such as a drug. Agent dispenser 112 operates in the same manner as agent dispenser 28 (FIGS. 1 and 2).

Membrane 114 has an upper end 122 provided with a lateral flange 124 which is annular and which presents a shoulder for the ledge 126 on the inner surface of the resilient wall 128 forming the outer peripheral margin of closure 110.

Bag 118 is formed from an elastomer material so that it is resilient. Bag 118 has an upper end 130 provided with a first lower surface which abuts the upper, flat, annular face of sleeve 116 to form an interface 132. End 130 also has a lateral flange 134 which overlies the upper, flat end face of membrane 114 as shown in FIG. 3. The resulting interfaces 132, 133 and 135 provide an effective seal which prevents the flow of agent into or out of reservoir 120 past closure 110.

Closure 110 has a main body 136 which has a beveled outer surface 138 provided with annular, transversely semi-circular ribs or beads 140 which, when closure 110 is in place closing the open end of agent dispenser 112, engage and depress the inner surface 142 of end 130 of bag 118. Thus, beads 140 provide additional sealing surfaces. Moreover, the annular flange 144 which interconnects body 136 with wall 128 presents an interface 146 which also adds to the sealing effect. When body 136 is forced into dispenser 112, the body 136 which is also of resilient material, such as rubber or the like, is biased inwardly by the resilience of upper end 130 of bag 118. The bias forces exerted on body 136 by end 130 tends to compress body 136, thereby keeping it frictionally engaged with the inner surface 142 of end 130 of bag 118.

Body 136 has a central bore 148 therethrough to allow a tube to be inserted into the reservoir 120. Such a tube is of the type shown in FIG. 4 and denoted by the numeral 150, the tube being carried by a crescent-shaped member 154 which also fits on the upper surface 156 of body 136 of closure 110. Tube 150 has a spherical enlargement 158 (FIG. 4) which is received within a spherical recess 160 in body 136 near surface 156 thereof.

Figure 4:
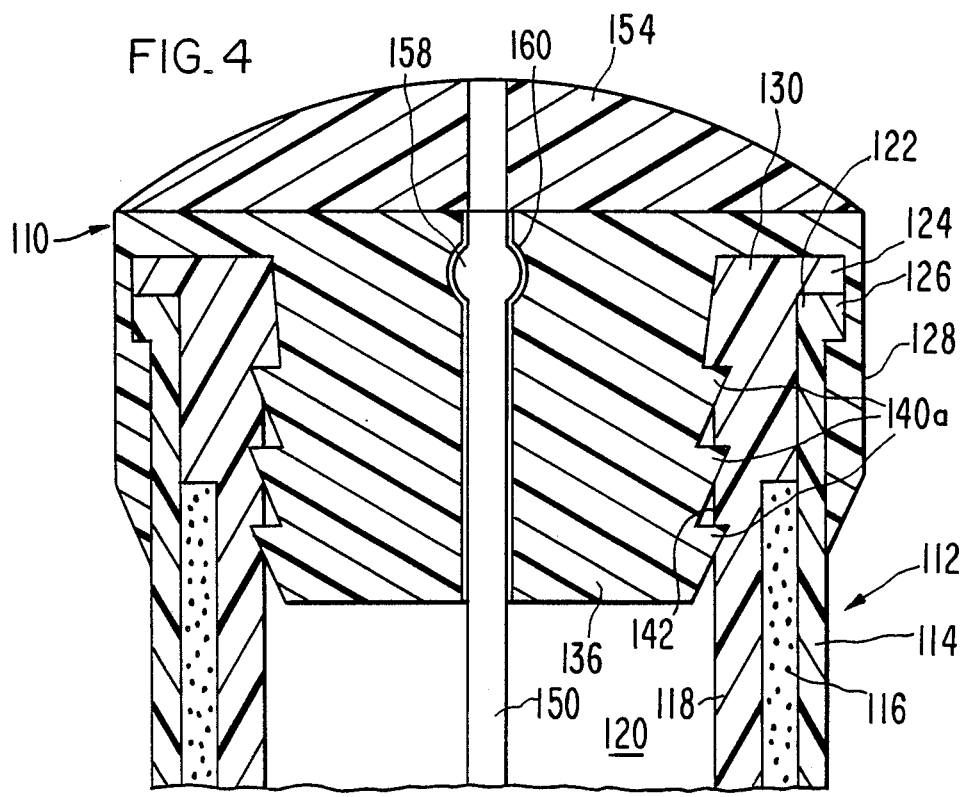

FIG. 4 shows a slightly modified form of closure 110 for closing the open end of agent dispenser 112. Instead of annular ribs 140, as shown in FIG. 3, closure 110 has annular sawtooth projections 140a which frictionally engage and compress the resilient inner surface 142 of end 130 of bag 118. All other components of closure 110 and dispenser 112 shown in FIG. 4 are essentially the same as corresponding components shown in FIG. 3.

We claim:

1. In an osmotically driven agent dispenser including an inner flexible bag adapted to contain the agent and having an open end, an intermediate layer of an osmotically effective solute composition at least partly encapsulating the bag, an outer shape-retaining membrane encapsulating the layer of osmotically effective solute composition, said membrane being at least in part permeable to water, and a port that extends from the interior of the bag to the exterior of the dispenser through which the agent may be charged into the bag and dispensed from the bag, the improvement comprising a locking snap-on closure for closing the open end of the bag, the closure having a biasing member for sealingly engaging the open end of the bag and a locking means preventing removal of the closure when the closure is in sealing engagement with the open end of the bag.

2. The agent dispenser as set forth in claim 1, wherein the agent is a fluid.

3. The agent dispenser as set forth in claim 1, wherein the closure comprises two biasing members for receiving the open end of the bag therebetween, the biasing members being resilient and biased toward one another.

4. The agent dispenser as set forth in claim 1, wherein the locking means comprises a ledge on the biasing member, the ledge adapted for underlying a shoulder on the outer shape-retaining membrane when the open end of the bag is placed in sealing relation with the closure.

5. The agent dispenser as set forth in claim 1, wherein the closure includes an inner biasing member and an outer biasing member, the inner biasing member including a wall having a central recess therein, the closure further including a plug receivable in the central recess and biasing the wall toward the outer biasing member.

6. The agent dispenser as set forth in claim 5, wherein the plug is comprised of a resilient material.

7. The agent dispenser as set forth in claim 5, wherein the wall has a taper, the outer surface of the plug being tapered and complemental to the taper of the wall.

8. The agent dispenser as set forth in claim 5, including a web on the inner biasing member for defining an inner boundary of the central recess, the web being integral with the wall, the agent charging and dispensing port extending through the web and the plug.

9. The agent dispenser as set forth in claim 6, wherein the plug has an outer surface provided with additional locking means thereon.

10. The agent dispenser as set forth in claim 9, wherein the additional locking means includes a plurality of spaced annular ribs.

11. The agent dispenser as set forth in claim 10, wherein each rib has a convex outer surface.

12. The agent dispenser as set forth in claim 10, wherein each rib has a sawtooth transverse cross section.

13. The agent dispenser as set forth in claim 5, wherein the closure includes a resilient flange connecting the inner and outer biasing members.

14. In an osmotically driven fluid dispenser comprising an inner flexible bag adapted to contain the fluid, an intermediate layer of an osmotically effective solute composition at least partly encapsulating the bag, an outer, generally rigid membrane casing encapsulating the layer of osmotically effective solute composition, said membrane being at least in part permeable to water, and a port that extends from the interior of the bag to the exterior of the dispenser through which the fluid may be charged into the bag and dispensed from the bag, the improvement comprising a snap-on closure for closing the open end of the bag, the closure having inner and outer biasing members for receiving and sealing the open end of the bag therebetween and a locking means preventing removal of the closure when the closure is in sealing engagement with the open end of the bag.

15. The fluid dispenser as set forth in claim 14, wherein the inner and outer biasing members have a space therebetween for receiving the open ends of the bag and the membrane.

16. The fluid dispenser as set forth in claim 14, wherein the members are resilient and are biased toward each other.

17. The fluid dispenser as set forth in claim 14, wherein the locking means comprises a ledge on one of the biasing members and a shoulder on the membrane casing, said ledge engaging the shoulder to lock the closure onto the casing.

18. The fluid dispenser as set forth in claim 14, wherein the inner biasing member includes a wall having a central recess therein, the closure further including a plug receivable in the central recess and biasing the inner wall outwardly toward the outer biasing member.

19. The fluid dispenser as set forth in claim 18, wherein the plug is comprised of a resilient material.

20. The fluid dispenser as set forth in claim 18, wherein the wall has a taper, the outer surface of the plug being tapered and complemental to the taper of the wall.

21. The fluid dispenser as set forth in claim 18, including a web for defining an inner boundary of the central recess, the web being integral with the wall, the charging and dispensing port extending through the web and the plug.

22. The fluid dispenser as set forth in claim 19, wherein the plug has an outer surface provided with additional locking means thereon.

23. The fluid dispenser as set forth in claim 22, wherein the additional locking means includes a plurality of spaced annular ribs.

24. The fluid dispenser as set forth in claim 23, wherein each rib has a convex outer surface.

25. The fluid dispenser as set forth in claim 23, wherein each rib has a sawtooth cross section.

26. The fluid dispenser as set forth in claim 14, wherein the closure includes a resilient flange connecting the inner and outer biasing members.

* * * * *